US009187463B2

(12) United States Patent
Numata et al.

(10) Patent No.: US 9,187,463 B2
(45) Date of Patent: Nov. 17, 2015

(54) POLYMORPH FORM OF 4-{[4-({[4-(2,2,2-TRIFLUOROETHOXY)-1,2-BENZISOXAZOL-3-YL]OXY}METHYL) PIPERIDIN-1-YL]METHYL}-TETRAHYDRO-2H-PYRAN-4-CARBOXYLIC ACID (75) Inventors: Toyoharu Numata, Aichi (JP); Hirohide Noguchi, Aichi (JP); Nobuaki Waizumi, Osaka (JP); Takashi Kojima, Kanagawa (JP)

(73) Assignee: RAQUALIA PHARMA INC., Aichi (JP)

(*) Notice: Subject to any disclaimer, the term of this patent is extended or adjusted under 35 U.S.C. 154(b) by 0 days.

(21) Appl. No.: 14/118,377

(22) PCT Filed: May 18, 2012

(86) PCT No.: PCT/JP2012/003288
§ 371 (c)(1),
(2), (4) Date: Jan. 16, 2014

(87) PCT Pub. No.: WO2012/157288
PCT Pub. Date: Nov. 22, 2012

(65) Prior Publication Data
US 2014/0187583 A1    Jul. 3, 2014

(30) Foreign Application Priority Data
May 18, 2011 (JP) .................. 2011-111901

(51) Int. Cl.
C07D 413/14    (2006.01)
(52) U.S. Cl.
CPC .................. *C07D 413/14* (2013.01)

(58) Field of Classification Search
CPC ..... C07D 413/14; A61P 43/00; A61K 31/454
USPC .......................................... 514/321; 546/198
See application file for complete search history.

(56) References Cited

U.S. PATENT DOCUMENTS

| 6,106,864 A | 8/2000 | Dolan et al. |
| 2008/0207690 A1 | 8/2008 | Noguchi et al. |

FOREIGN PATENT DOCUMENTS

| JP | 2008-531539 A | 8/2008 |
| WO | WO-9111172 A1 | 8/1991 |
| WO | WO-9402518 A1 | 2/1994 |
| WO | WO-9855148 A1 | 12/1998 |
| WO | WO-0035298 A1 | 6/2000 |
| WO | WO-2006090224 A1 | 8/2006 |
| WO | WO-2011101774 A1 | 8/2011 |

OTHER PUBLICATIONS

International Search Report in corresponding PCT/JP2012/003288 dated Jun. 12, 2012.
Written Opinion in corresponding PCT/JP2012/003288 dated Jun. 12, 2012.
(Continued)

*Primary Examiner* — Janet L Andres
*Assistant Examiner* — Daniel Carcanague
(74) *Attorney, Agent, or Firm* — Marshall, Gerstein & Borun LLP (57) ABSTRACT The present invention relates to novel crystal forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid. More particularly, the invention relates to polymorph forms (Polymorph Form I or Polymorph Form II), and to processes for the preparation of, compositions containing and to uses of, such polymorph forms.

10 Claims, 3 Drawing Sheets (56) References Cited

OTHER PUBLICATIONS

Liang et al., "Fast-dissolving Intraoral Drug Delivery Systems," *Expert Opinion Therapeutic Patents*, pp. 981-986 (2001).
Lieberman et al., "Pharmaceutical Dosage Forms," *Marcel Dekker, Inc.*, (1980).
Verma et al., "Current Status of Drug Delivery Technologies and Future Directions," *Pharmaceutical Technology On-Line*, pp. 1-14 (2001).
Finnin et al., "Transdermal Penetration Enhancers: Applications, Limitations, and Potential," *Journal of Pharmaceutical Sciences*, pp. 955-958 (1999).
Evrard et al., "Cyclodextrins as a Potential Carrier in Drug Nebulization," *Journal of Controlled Release 96*, pp. 403-410 (2004).
Bockaert et al., "The 5-HT4 Receptor: A Place in the Sun," *TiPS*, pp. 141-145 (1992).
Ford et al., "The 5-HT4 Receptor," *Medical Research Reviews*, pp. 633-662 (1993).
Gullikson et al., "Gastrointestinal Motility Responses to the S and R Enantiomers of Zacopride, a 5-HT4 Agonist and 5-HT3 Antagonist," *Drug Development Research*, pp. 405-417 (1992).
Eglen et al., "Central 5-HT4 Receptors," *TiPS*, pp. 391-398 (1995).
Bockaert et al., "5-HT4 Receptors Potential Therapeutic Implications in Neurology and Psychiatry," *CNS Drugs 1*, pp. 6-15 (1994).
Romanelli et al., "Synthesis and Biological Activity of a Series of Aryl Tropanyl Esters and Amides Chemically Related to 1H-Indole-3-carboxylic Acid endo 8-Methyl-8-azabicyclo[3.2.1]oct-3-yl Ester," *Arzheim Forsch./Drug Res. 43*, pp. 913-918 (1993).
Kaumann et al., "A 5-HT4-like Receptor in Human Right Atrium," *Naunyn-Schmiedebergs Archives of Pharmacology*, pp. 150-159 (1991).
"Remington: The Science and Practice of Pharmacy," *Mack Publishing Company*, Nineteenth Edition (1980).
"Remington's Pharmaceutical Sciences," *Mack Publishing Company*, Eighteenth Edition (1990).
International Preliminary Report on Patentability in corresponding PCT/JP2012/003288 dated Feb. 25, 2013.
M. R. Caira, "Crystalline Polymorphism of Organic Compounds," Department of Chemistry, vol. 198, pp. 163-208 (1998).
Extended European Search Report in corresponding PCT/JP2012/003288 dated Aug. 29, 2014.

POLYMORPH FORM OF 4-{[4-({[4-(2,2,2-TRIFLUOROETHOXY)-1,2-BENZISOXAZOL-3-YL]OXY}METHYL)PIPERIDIN-1-YL]METHYL}-TETRAHYDRO-2H-PYRAN-4-CARBOXYLIC ACID

TECHNICAL FIELD

The present invention relates to novel crystal forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid.

More particularly, the invention relates to polymorph forms (Polymorph Form I and Polymorph Form II), and to processes for the preparation of, compositions containing and to uses of, such polymorphs.

BACKGROUND ART

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid is disclosed in WO2006/090224 as a 5-HT4 receptor antagonist, which is useful in the treatment or alleviation of disease conditions mediated by 5-HT4 receptor activity; in particular 5-HT4 receptor agonistic activity, such as gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome (See {NPL 1} TiPs, 1992, 13, 141; {NPL 2} Ford A. P. D. W. et al., Med. Res. Rev., 1993, 13, 633; {NPL 3} Gullikson G. W. et al., Drug Dev. Res., 1992, 26, 405; {NPL 4} Richard M. Eglen et al, TiPS, 1995, 16, 391; {NPL 5} Bockaert J. et al., CNS Drugs, 1, 6; {NPL 6} Romanelli M. N. et al., Arzheim Forsch./Drug Res., 1993, 43, 913; and {NPL 7} Kaumann A. et al., Naunyn-Schmiedeberg's. 1991, 344, 150-59).

The previously known methods of preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid, described in WO2006/090224, have produced simply an white solid, which is not a crystal or mixture of other crystal forms.

CITATION LIST

Patent Literature

{PL 1} WO2006/090224
{PL 2} U.S. Pat. No. 6,106,864
{PL 3} WO 00/35298
{PL 4} WO 91/11172
{PL 5} WO 94/02518
{PL 6} WO 98/55148.

Non Patent Literature

{NPL 1} Bockaert J. et al., TiPs 13; 141-45, 1992
{NPL 2} Ford A. P et al., Med. Res. Rev. 13: 633-62, 1993
{NPL 3} Gullikson G. W. et al., Drug Dev. Res. 26; 405-17, 1992
{NPL 4} Richard M. Eglen et al., TiPs 16; 391-98, 1995
{NPL 5} Bockaert J. et al., CNS Drugs 1; 6-15, 1994
{NPL 6} Romanelli M. N. et al., Arzheim Forsch./Drug Res., 43; 913-18, 1993
{NPL 7} Kaumann A. J. et al., Naunyn-Schmiedebergs Arch Pharmacol., 344; 150-59, 1991
{NPL 8} Remington's Pharmaceutical Sciences, 19th Edition (Mack Publishing Company, 1995)
{NPL 9} Expert Opinion in Therapeutic Patents, 11 (6), 981-986, by Liang and Chen (2001).
{NPL 10} Tablets, Vol. 1, by H. Lieberman and L. Lachman (Marcel Dekker, New York, 1980).
{NPL 11} Pharmaceutical Technology On-line, 25(2), 1-14, by Verma et al. (2001)
{NPL 12} J Pharm Sci, 88 (10), 955-958, by Finnin and Morgan (October 1999).
{NPL 13} Evrard, B., et al., Journal of Controlled Release 96 (3), pp. 403-410, 2004.

SUMMARY OF INVENTION

Technical Problem

As well-known by skilled in the arts, it has been a desirable goal to find or prepare a crystalline or crystalline form in drug development from the various viewpoints including formulation and manufacturing of the drug (See Byrn S. R. et al., Solid-State Chemistry of Drugs 2nd ed., pp 3-43 and 461-503, 1999, SSCI, Inc.).

According to the line, great efforts have been made to find or prepare a crystalline or crystalline form of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid since the said compound was disclosed in 2006 (WO2006/090224) by Pfizer. For instance, esters such as ethyl acetate, alcohols such as methanol, ethanol and isopropyl alcohol, nitriles such as acetonitrile, ethers such as diethyl ether and MTBE (methyl t-butyl ether), ketones such as acetone and methyl ethyl ketone, halogenated hydrocarbons such as dichloromethane and chloroform were used as recrystallization solvents, but all of them resulted in failure.

In spite of such great efforts, no pharmaceutically suitable crystalline forms of the said compound have been identified yet.

As mentioned before, when ethyl acetate was used as a recrystallization solvent in a usual manner conducted by skilled in the arts, only unsuccessful results have been obtained. After an exhaustive and careful study, the inventors of the present invention have managed to find out a very special and unique condition of preparing the crystalline form using ethyl acetate, which can provide the much-anticipated crystalline form (Polymorph Form I) of the said compound.

As disclosed in the working example of the present invention, a white solid of the said compound was suspended in ethyl acetate for 1 day at 40° C. and 5 days at room temperature to afford to Polymorph Form I. Those skilled in the arts have never thought of such crystallization condition.

Then another crystalline (Polymorph Form II) has been also obtained from the Polymorph Form I obtained in the special condition. Polymorph Form I transforms to Polymorph Form II at 110° C. or higher temperature, but resulting Polymorph Form II converts to Polymorph Form I under measurement conditions such as nitrogen flow when cooling Polymorph Form II to room temperature. The inventors of the present invention also discovered a condition of obtaining Polymorph Form II at room temperature.

In addition, once the seed of the crystalline form is obtained, the same crystalline form can be easily obtained in a small scale synthesis. On large scale synthesis, temperature control is essential for preparing a pharmaceutically suitable crystalline form.

According to the line, it is an object of this invention to provide a pharmaceutically suitable crystalline forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid, which can be easily, economically and reproducibly prepared for use in a pharmaceutical formulation having consistent performance characteristics such as relating to stability and bioavailability. Also it is an object of this invention to provide processes for the preparation of, compositions containing and uses of, such polymorph forms.

Solution to Problem

Thus, the invention provides:

[1]
4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I, which is characterized by a powder X-ray diffraction pattern (PXRD) obtained by irradiation with Cu-Kα radiation which includes main peaks at 2-Theta° 5.9, 9.3, 9.8, 11.9, 13.7, 14.3, 15.0, 17.8, 18.2-19.3, 19.7, 22.6, 23.4-24.5 and 24.9+/−0.2;

[2]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described in [1], which is further characterized by differential scanning calorimetry (DSC) in which it exhibits an endothermic event at about 169° C.;

[3]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described in [1] or [2], which is further characterized by an infrared (IR) spectrum (KBr) which shows absorption bands at 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556+/−2 cm$^{-1}$;

[4]
4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II, which is characterized by a PXRD obtained by irradiation with Cu-Kα radiation which includes main peaks at 2-Theta° 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6+/−0.2;

[5]
4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II as described in [4], which is further characterized by DSC in which it exhibits an endothermic event at about 167-169° C.;

[6]
4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II, as described in [4] or [5], which is further characterized by an infrared (IR) spectrum (KBr) which shows absorption bands at 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555+/−2 cm$^{-1}$.

[7]
A pharmaceutical composition including 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [6], together with one or more pharmaceutically acceptable excipients;

[8]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [6] for use as a medicament;

[9]
The use of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [6], or a pharmaceutical composition as described in [7], in the preparation of a medicament for the curative, palliative or prophylactic treatment of disease conditions mediated by 5-HT4 receptor activity;

[10]
A method of treating disease conditions mediated by 5-HT4 receptor activity, which comprises administering an effective amount of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [6], or a pharmaceutical composition as described in [7], to an animal, including a human, in need of such treatment;

[11]
A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I as described in any one of [1] to [3], comprising the step of recrystallizing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid from an organic solvent including ethyl acetate; and

[12]
A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II as described in any one of [4] to [6], comprising the step of placing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid on 110° C. or higher temperature.

Advantageous Effects of Invention

It has now been surprisingly found that this object has been achieved by the present invention, which provides crystalline polymorphic forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid known as Polymorph Form I and Polymorph Form II, and an inventive process for the preparation of each thereof. Polymorph Form I and Polymorph Form II were found to be more stable than white solid disclosed in the prior art WO2006/090224. In addition, in terms of hygroscopicity both of them have a decided advantage over the white solid disclosed in the prior art WO2006/090224. Furthermore Polymorph Form of the present invention was found to be applicable for a large scale synthesis. Both of them are anhydrous crystal forms, and have acceptable solid-state properties for solid dosage form development.

DESCRIPTION OF EMBODIMENTS

Accordingly, the present invention provides crystalline 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I, which is characterized by a powder X-ray diffraction pattern (PXRD) obtained by irradiation with Cu-Kα radiation which includes main peaks at 2-Theta° 5.9, 9.3, 9.8, 11.9, 13.7, 14.3, 15.0, 17.8, 18.2-19.3, 19.7, 22.6, 23.4-24.5 and 24.9+/−0.2;

4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I as described above, which is further characterized by differential scanning calorimetry (DSC) in which it exhibits an endothermic thermal event at about 169° C., 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I as described above, which is yet further characterized by an infrared (IR) spectrum (KBr) which shows absorption bands at 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556+/−2 cm$^{-1}$;

4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II, which is characterized by a powder X-ray diffraction pattern (PXRD) obtained by irradiation with Cu-Kα radiation which includes main peaks at 2-Theta° 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6+/−0.2;

4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II as described above, which is further characterized by differential scanning calorimetry (DSC) in which it exhibits an endothermic event at about 167-169° C.; and 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II, as described above, which is further characterized by an infrared (IR) spectrum (KBr) which shows absorption bands at 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555+/−2 cm$^{-1}$.

As a further aspect of the invention, there is provided 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention for use as a medicament.

As a yet further aspect of the invention, there is provided the use of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention in the manufacture of a medicament for the treatment of any disease for which a 5-HT4 receptor antagonist is indicated, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

As an alternative aspect, there is provided a method for the treatment of any disease for which a 5-HT4 receptor antagonist is indicated, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome, including administration of a therapeutically effective amount of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention to an animal, including a human, in need of such treatment.

The 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid Polymorph Form of the present invention is useful for the general treatment of disease conditions mediated by 5-HT4 receptor activity.

The 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid Polymorph Form of the present invention may also be useful for the treatment of a disorder or condition selected from the group consisting of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

Synthetic routes for the preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid are described in WO2006/090224 and in Example Section below.

4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I may be prepared by crystallization from a solution of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid in ethyl acetate.

Organic solvents including ethyl acetate can be used for the crystallization of Polymorph Form I. Preferably examples of solvents which can be mixed with ethyl acetate include one or more than one solvents selected from: water, alcohols such as methanol, ethanol, and propanol; ethers such as diethyl ether, tert-butylmethyl ether, dioxane, and tetrahydrofuran; hydrocarbons such as hexane, heptane, cyclohexane, dichloromethane, chloroform, benzene, toluene, and xylene; ketones such as acetone and methylethylketone; amides such as dimethylformamide and dimethylacetamide; and sulfoxides such as dimethylsulfoxide.

Depending on the concentration of the compound, the reducing rate of temperature at the recrystallization is generally lower than 100° C./hour at the concentration of about 0.1 mg/mL to about 200 mg/mL. Preferably lower than 50° C./hour, more preferably lower than 20° C./hour, and most preferably lower than 5° C./hour can be applied for the recrystallization.

The 4-{[4-({[4-(2,2,2-trifluoroethoxy)-1,2-benzisoxazol-3-yl]oxy}methyl)piperidin-1-yl]-methyl}tetrahydro-2H-pyran-4-carboxylic acid Polymorph Form of the present invention can be administered alone or in combination with one or more other drugs (or as any combination thereof). Generally, they will be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Thus, as a further aspect of the present invention, there is provided a pharmaceutical composition including 4-{[4-({[4-(2,2,2-trifluoroethoxy)-1,2-benzisoxazol-3-yl]oxy}methyl)-piperidin-1-yl]methyl}tetrahydro-2H-pyran-4-carboxylic acid Polymorph Form and one or more suitable excipients. The composition is suitable for the treatment of disease conditions mediated by 5-HT4 receptor activity.

The term "Polymorph Form", as used herein, includes Polymorph Form I and/or Polymorph Form II.

Weight purity of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I of the present invention is not limited, but preferably an essentially pure Polymorph Form can be used for specific embodiments in this invention.

For the avoidance of doubt, the expression 'essentially pure' when used herein means at least 90% by weight purity. More preferably, 'essentially pure' means at least 95% by weight purity and most preferably means at least 98% by weight purity.

References herein to "treatment" include references to curative, palliative and prophylactic treatment.

For non-human animal administration, the term 'pharmaceutical' as used herein may be replaced by 'veterinary.'

Pharmaceutical compositions suitable for the delivery of Polymorph Form of the invention and methods for the preparation will be readily apparent to those skilled in the art. Such compositions and methods for the preparation may be found, for example, in Remington's Pharmaceutical Sciences, 19th Edition (Mack Publishing Company, 1995).

Oral Administration

Polymorph Form of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Polymorph Form of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a Polymorph Form in accordance with the invention, a film-forming polymer, a binder, a solvent, a humectant, a plasticizer, a stabilizer or emulsifier, a viscosity-modifying agent and a solvent. Some components of the formulation may perform more than one function.

Polymorph Form of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, Polymorph Form of the invention may be in the form of multiparticulate beads.

The film-forming polymer may be selected from natural polysaccharides, proteins, or synthetic hydrocolloids and is typically present in the range of 0.01 to 99 weight %, more typically in the range of 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper.

This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al. (2001). The use of chewing gum to achieve controlled release is described in WO 00/35298.

Parenteral Administration

The Polymorph Form of the invention may also be administered directly into the blood stream, into muscle, or into an internal organ. Suitable means for parenteral administration include intravenous, intraarterial, intraperitoneal, intrathecal, intraventricular, intraurethral, intrastemal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus the Polymorph Form of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(lactic-co-glycolic acid) (PLGA) microspheres.

Topical Administration

The Polymorph Form of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject (trade mark), Bioject (trade mark), etc.) injection. Topical administration may also be achieved using a patch, such as a transdermal iontophoretic patch.

Formulations for topical administration may be formulated to be immediate and/or modified release. Modified release formulations include delayed-, sustained-, pulsed-, controlled-, targeted and programmed release.

The Polymorph Form of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of a Polymorph Form in accordance with the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as/-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 micro g to 20 mg of the compound of the invention per actuation and the actuation volume may vary from 1 micro L to 100 micro L. A typical formulation may comprise a Polymorph Form in accordance with the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PLGA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 micro g to 20 mg of the compound. The overall daily dose will typically be in the range of 1 micro g to 100 mg which may be administered in a single dose or, more usually, as divided doses throughout the day.

Rectal/Intravaginal Administration

Polymorph Form of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

Polymorph Form of the invention may also be administered directly to the eye or ear, typically in the form of drops of a micronized suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gellan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Polymorph Form of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Publication Nos. WO 91/11172, WO 94/02518, WO 98/55148 and Evrard, B., et al., Journal of Controlled Release 96 (3), pp. 403-410, 2004.

Dosage

For treating or preventing gastrointestinal diseases, a suitable dosage level of Polymorph Form of this invention is about 0.0001 to 1000 mg per day, preferably about 0.001 to 100 mg per day, and more preferably about 0.005 to 50 mg per day, of the active compound. The compounds may be administered on a regimen of 1 to 4 times per day. In some cases, however, a dosage outside these limits may be used.

These dosages are based on an average human subject having a weight of about 60 kg to 70 kg. The physician will readily be able to determine doses for subjects whose weight falls outside this range, such as infants and the elderly. For the avoidance of doubt, references herein to "treatment" include references to curative, palliative and prophylactic treatment.

Polymorph Form of the present invention may also optionally be combined with another pharmacologically active compound, or with two or more other pharmacologically active compounds, particularly for the treatment of disease conditions mediated by 5-HT4 receptor activity. For example, the Polymorph Form of the present invention, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g.

(alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;

a vanilloid receptor agonist (e.g. resiniferatoxin) or antagonist (e.g. capsazepine);

a transient receptor potential cation channel subtype (V1, V2, V3, V4, M8, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol(registered trademark);

a PDEV inhibitor, such as

5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3 alpha,5alpha)(3-aminomethyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, buprorion, buprorion metabolite hydroxybuprorion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as
S-[2-[(1-iminoethyl)amino]ethyl]-L-homocysteine,
S-[2-[(1-iminoethyl)-amino]ethyl]-4,4-dioxo-L-cysteine,
S-[2-[(1-iminoethyl)amino]ethyl]-2-methyl-L-cysteine,
(2S,5Z)-2-amino-2-methyl-7-[(1-iminoethyl)amino]-5-heptenoic acid,
2-[[(1R,3S)-3-amino-4-hydroxy-1-(5-thiazolyl)-butyl]thio]-5-chloro-3-pyridinecarbonitrile;
2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]
thio]-5-thiazolebutanol,
2-[[(1R,3S)-3-amino-4-hydroxy-1-(5-thiazolyl)butyl]thio]-
6-(trifluoromethyl)-3 pyridinecarbonitrile,
2-[[(1R,3S)-3-amino-4-hydroxy-1-(5-thiazolyl)butyl]thio]-
5-chlorobenzonitrile,
N-[4-[2-(3-chlorobenzylamino)ethyl]phenyl]thiophene-2-
carboxamidine, or guanidinoethyldisulfide;
an acetylcholinesterase inhibitor such as donepezil;
a prostaglandin E2 subtype 4 (EP4) antagonist such as
N-[({2-[4-(2-ethyl-4,6-dimethyl-1H-imidazo[4,5-c]pyridin-
1-yl)phenyl]ethyl}amino)-carbonyl]-4-methylbenzene-
sulfonamide or
4-[(1S)-1-({[5-chloro-2-(3-fluorophenoxy)pyridin-3-yl]
carbonyl}amino)ethyl]benzoic acid;
a leukotriene B4 antagonist; such as
1-(3-biphenyl-4-ylmethyl-4-hydroxy-chroman-7-yl)-cyclo-
pentanecarboxylic acid (CP-105696),
5-[2-(2-Carboxyethyl)-3-[6-(4-methoxyphenyl)-5E-hex-
enyl]oxyphenoxy]-valeric acid (ONO-4057) or DPC-
11870,
a 5-lipoxygenase inhibitor, such as zileuton,
6-[(3-fluoro-5-[4-methoxy-3,4,5,6-tetrahydro-2H-pyran-4-
yl])phenoxy-methyl]-1-methyl-2-quinolone (ZD-2138),
or
2,3,5-trimethyl-6-(3-pyridylmethyl),1,4-benzoquinone (CV-
6504);
a sodium channel blocker, such as lidocaine;
a calcium channel blocker, such as ziconotide, zonisamide,
mibefradil;
a 5-HT3 antagonist, such as ondansetron;
a chemotherapy drug such as oxaliplatin, 5-fluorouracil,
leukovolin, paclitaxel;
a calcitonin gene related peptide (CGRP) antagonist;
a bradykinin (BK1 and BK2) antagonist;
a voltage-gated sodium-dependent channel blocker
($Na_{v1.3}$, $Na_{v1.7}$, $Na_{v1.8}$);
a voltage dependent calcium channel blocker (N-type,
T-type);
a P2X (ion channel type ATP receptor) antagonist;
an acid-sensing ion channel (ASIC1a, ASIC3) antagonist;
and the pharmaceutically acceptable salts and solvates
thereof.

Such combinations offer significant advantages, including synergistic activity, in therapy.

Combination Drug and Kit

One embodiment of the present invention is a combination of Polymorph Form of the present invention, and a drug for gastrointestinal diseases. A "combination" according to the invention may be present as a "fix combination" or as a "kit of parts combination". A "fix combination" is defined as a combination wherein the (i) at least one drug for gastrointestinal diseases and (ii) Polymorph Form are present in one unit. A "kit of parts combination" is defined as a combination wherein the (i) at least one drug for gastrointestinal diseases and (ii) Polymorph Form are present in more than one unit. The components of the "kit of parts combination" may be administered simultaneously, sequentially or separately. The molar ratio of the drug for gastrointestinal diseases to Polymorph Form used according to the invention is within the range of from 1:100 to 100:1, such as from 1:50 to 50:1 or from 1:20 to 20:1 or from 1:10 to 10:1. The two drugs may be administered separately in the same ratio. Examples are other 5-HT4 agonists, proton pump inhibitors, H2 receptor antagonists, and drugs for IBS or constipations. These examples are H2 blocking agents such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

The present invention extends to a combination comprising 4-{[4-({[4-(2,2,2-trifluoroethoxy)-1,2-benzisoxazol-3-yl] oxy}methyl)piperidin-1-yl]methyl}-tetrahydro-2H-pyran-4-carboxylic acid Polymorph Form I and/or Polymorph Form II and one or more therapeutic agents, such as those listed above, for simultaneous, separate or sequential use in the curative, prophylactic or palliative treatment of disease conditions mediated by 5-HT4 receptor activity.

EXAMPLES

The following example is for reference only.
Analysis
Powder X-Ray Diffraction (PXRD)

The PXRD analyses are performed using a Rigaku RINT-TTR X-ray powder diffractometer using Cu-Kα radiation. The samples can also be measured under the high/low temperature condition by using the attachment of the variant-temperature sample holder. The instrument is equipped with a fine focus X-ray tube. The tube voltage and amperage are set to 50 kV and 300 mA respectively. The divergence and scattering slits are set at 0.25° and the receiving slit is set at 0.15 mm. Diffracted radiation is detected by a NaI scintillation detector. A theta-two theta continuous scan at 4°/min (step size 0.02°) from 3 to 40 2-Theta° is used. A silicon standard is analyzed to check the machine alignment. Data are collected and analyzed using-Rigaku X-ray system. Samples are prepared for analysis by placing them in an aluminum sample holder that is horizontally rotated at 60 rpm during data acquisition.

Thermogravimetry/Differential Thermal Analysis (TG/DTA)

TG/DTA is performed using Seiko 6200R system. The sample is placed into an aluminum TG/DTA pan. Each sample is heated under a nitrogen purge at a rate of 5° C./min, up to a final temperature of 300° C. Reported values are rounded and should therefore be considered approximate.

Differential Scanning Calorimetry (DSC)

DSC analysis is performed using Seiko DSC 6200R or Mettler Toledo DSC822. The sample is placed into an aluminum DSC pan and the weight accurately recorded. The pan is covered with a lid and then crimped. Each sample is heated under a nitrogen purge at a rate of 5° C./min, up to a final temperature of 220 or 200° C. Indium metal is used as the calibration standard. Reported values are rounded and should therefore be considered approximate.

FT-IR Spectroscopy

Infrared spectra are acquired on a Shimadzu IRPrestage-21 (FT-IR) spectrophotometer equipped with a black-coated heated wire beam source, a Germanium coated on potassium bromide (KBr) beamsplitter, and a high sensitivity pyroelectric detector (DLATGS). Each spectrum represents 40 co-added scans collected at a spectral resolution of 4 $cm^{-1}$. Sample preparation consisted of placing the KBr disk, prepared from the sample and KBr. A background data set is acquired with a blank disk of KBr without samples. A Log MR (R=reflectance) spectrum is acquired by taking a ratio of these two data sets against each other. Wavelength calibration is performed using polystyrene. Reported values are rounded and should therefore be considered approximate.

Hygroscopicity Study by Dynamic Vapor Sorption Analysis (DVS)

Hygroscopicity study is performed using Surface Measurement Systems DVS-1. The sample is placed on a microbalance in the instrument. After the sample is dried under 0% humidity environment at 25° C., relative humidity is raised to 95% RH at 5% RH increments, maintaining the sample at each step until equilibration had been attained. After completion of the sorption cycle, the sample is dried to 10% RH using the same procedure (desorption cycle). The weight change during the sorption/desorption cycle is monitored, allowing for the hygroscopic nature of the sample to be determined.

Example 1

Preparation of 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid according to the conventional process A mixture of methyl 4-{[4-({[4-(2,2,2-trifluoroethoxy)-1,2-benzisoxazol-3-yl]oxy}methyl)piperidin-1-yl]methyl}-tetrahydro-2H-pyran-4-carboxylate (89 mg, 0.18 mmol, PCT WO2006090224 EXAMPLE 1, Step 5) in tetrahydrofuran (1 mL), methanol (1 mL) and 2 N aq. sodium hydroxide (1 mL) is stirred at 70° C. for 17 h. The mixture is neutralized with 2 N hydrochloric acid (1 mL) and formed precipitate is filtered. The precipitate is triturated with diethylether to give 50 mg (58%) of the title compound as a white solid.

$^1$H-NMR (DMSO-d$_6$) delta: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.19 (2H, d, J=5.9 Hz), 3.75-3.62 (2H, m), 3.48-3.30 (2H, m), 2.90-2.74 (2H, m), 2.50 (2H, s), 2.29-2.13 (2H, m), 1.94-1.23 (9H, m).

A signal due to $CO_2H$ is not observed.
MS (ESI) m/z: 473 (M+H)$^+$, 471 (M−H)$^-$.
IR (KBr) v: 2950, 1617, 1527, 1188, 1113 cm$^{-1}$.
Anal. Calcd for $C_{22}H_{27}N_2O_6F_3$: C, 55.93; H, 5.76; N, 5.93. Found: C, 55.72; H, 5.78; N, 5.80.

Example 2

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I A mixture of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid (40 mg, 0.085 mmol) is dissolved in 1,4-dioxane (2 mL) by sonication and vortex mixing, and then frozen in a freezer at −40° C. for several hours. The resultant mixture is dried in vacuo overnight to give a freeze-dried amorphous solid. Ethyl acetate (0.8 mL) is added to the sample and the mixture is heated to 65° C. for dissolution. The resultant solution is gradually cooled to room temperature over 3 days. The precipitate is collected by filtration and dried to afford 27 mg of the white solid. Then a part of the white solid is suspended in ethyl acetate for 1 day at 40° C. and 5 days at room temperature to afford a crystalline form of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid.

Figure 2:
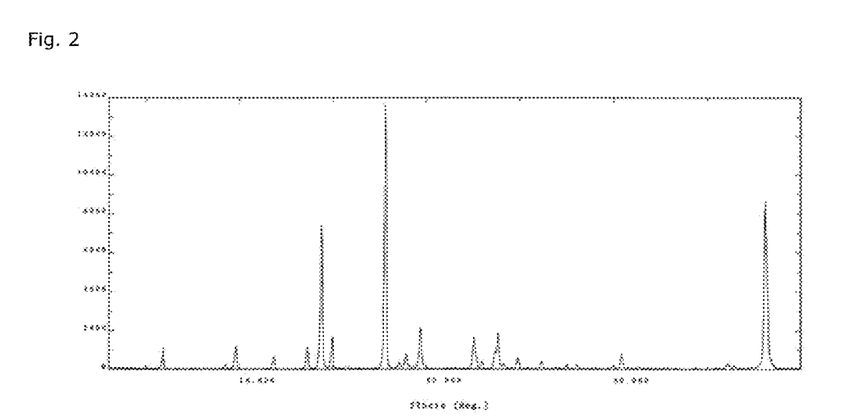
FIG. 2 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I.

The same signals are observed in $^1$H-NMR and MS spectra.
m.p. (DSC onset): 169° C.
Crystallinity by PXRD: Crystal (FIG. 2). Main peaks at 2-Theta°: 5.9, 9.3, 9.8, 11.9, 13.7, 14.3, 15.0, 17.8, 18.2-19.3, 19.7, 22.6, 23.4-24.5 and 24.9. Each peak has a margin of error of +/−0.2.

IR (KBr) v: 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556 cm$^{-1}$. Each peak has a margin of error of +/−2 cm$^{-1}$.
Anal. Calcd for $C_{22}H_{27}N_2O_6F_3$: C, 55.93; H, 5.76; N, 5.93. Found: C, 56.10; H, 5.75; N, 5.99.

Example 3

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I A slurry of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid (1.326 kg, 2.807 mol, a white solid) in ethyl acetate (18.564 L) is dissolved at 70° C. The solution is cooled to 64° C. during 35 min and 200 mg of a seed of Polymorph Form I (0.423 mmol) is added to the mixture. The mixture is cooled to 40° C. over 5 h period and stirred at this temperature for 14.5 h. The slurry is gradually cooled to 19° C. during 6 h period and the mixture is stirred at this temperature for 46 h. The formed precipitate is collected by filtration and the filter cake is washed with 2.0 L of ethyl acetate. The filter cake is dried under reduced pressure at 50° C. to afford 1.140 kg of the desired crystalline form of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid (86%).
Anal. Calcd for $C_{22}H_{27}N_2O_6F_3$: C, 55.93; H, 5.76; N, 5.93. Found: C, 55.76; H, 5.74; N, 5.85.

The other analytical data are same as those in the above EXAMPLE 2.

Example 4

Figure 3:
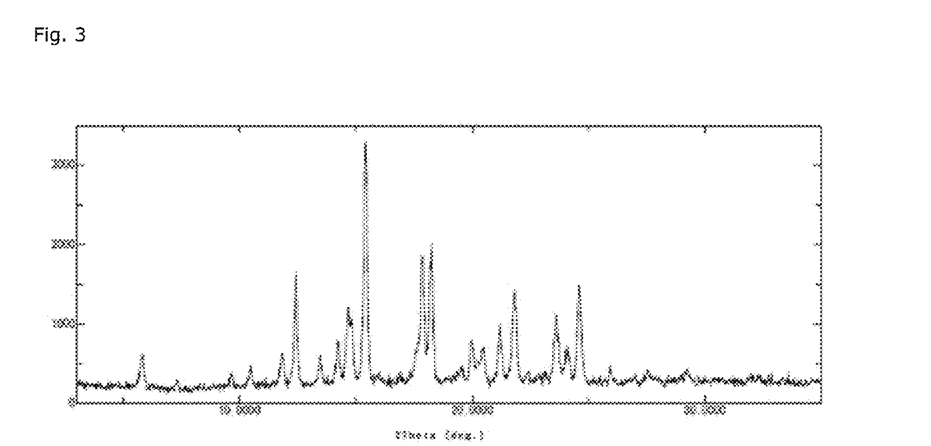
FIG. 3 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II.
Figure 4:
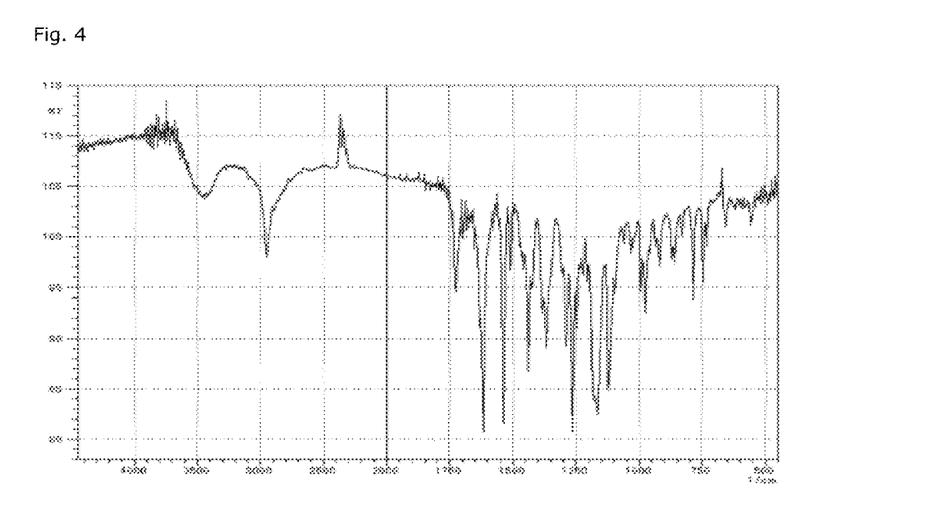
FIG. 4 shows the IR spectra of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I.
Figure 5:
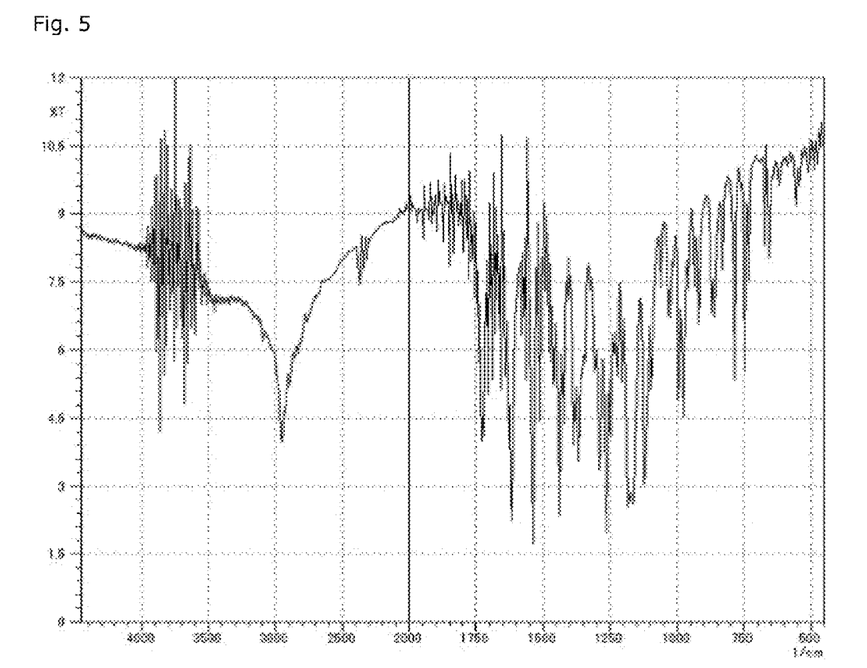
FIG. 5 shows the IR spectra of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II.

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II Preparation Method 1)
Polymorph Form I begins to transform to Polymorph Form II at around 110° C.
Preparation Method 2)
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I (5 mg) is placed on the temperature-variable sample holder of PXRD, and the temperature of the sample holder is raised to 120° C. and kept for 10 min., then cooled down to room temperature without nitrogen flow to the sample holder to afford Polymorph Form II of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid. Conversion to the Polymorph Form II is confirmed by in situ monitoring of PXRD spectrum.
m.p. (DSC onset): 167° C.
Crystallinity by PXRD: Crystal (FIG. 3). Main peaks at 2-Theta° 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6. Each peak has a margin of error of +/−0.2.
IR (KBr) v: 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555 cm$^{-1}$. Each peak has a margin of error of +/−2 cm$^{-1}$.

Example 5

In the hygroscopicity study by dynamic vapor sorption (DVS) analysis, Polymorph Form I absorbs less than 0.2 wt % under 90% relative humidity (RH) at 25° C. On the other hand, the white solid disclosed in the prior art WO2006/090224 absorbs 1.2 wt % and 5.5 wt % of water under 85% RH and 90% RH, respectively. The following table 1 shows that weight gain % of Polymorph Form I and the white solid disclosed in the prior art WO2006/090224.

TABLE 1

|  | 75% RH | 80% RH | 85% RH | 90% RH |
|---|---|---|---|---|
| Polymorph Form I | 0.15 | 0.15 | 0.15 | 0.18 |
| White solid disclosed in the prior art WO2006/090224 | 0.33 | 0.35 | 1.2 | 5.5 |

Example 6

Solid-state stability study is performed using Nagano Science Constant temperature/humidity control chamber LH-20-11M, LH-21-11M, LTL-200D3CJ-14 or LTX-01. The sample is placed in the chamber and exposed under 25° C./60% RH, 40° C./75% RH and/or irradiated with a Xenon lamp. The crystalline form, thermal behavior, purity and/or weight change of the resultant sample after the exposure or irradiation are evaluated by XRPD, TG/DTA or DSC, HPLC, microbalance analysis, respectively.

Polymorph Form is found to be stable.

Figure 1:
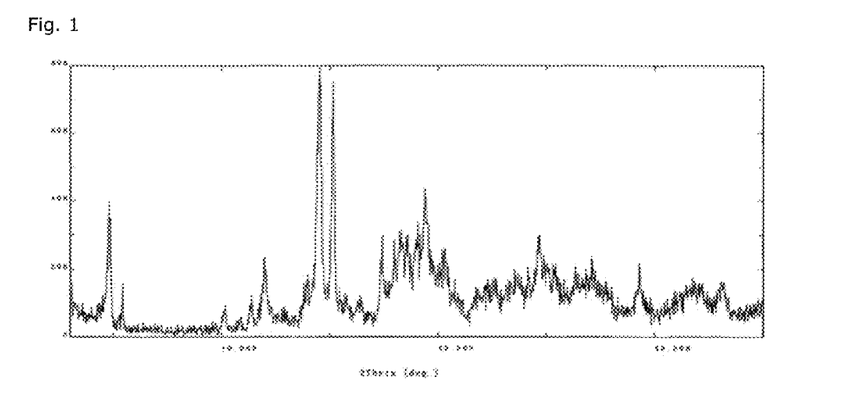
FIG. 1 shows the PXRD pattern of a reference product obtained from the method of preparing 4-{[4-({[4-(2,2,2- trifluoroethoxy)-1,2-benzisoxazol-3-yl]oxy}methyl)piperidin-1-yl]-methyl}-tetrahydro-2H-pyran-4-carboxylic acid described in Example 1 of WO2006/090224.

FIG. 1 shows the PXRD pattern of the reference product described in WO2006/090224. FIG. 2 shows the PXRD pattern of Polymorph Form I. FIG. 3 shows the PXRD pattern of Polymorph Form II.

As indicated by the comparison between FIG. 1, FIG. 2 and FIG. 3, neither Polymorph Form I nor Polymorph Form II corresponds to the reference product described in WO2006/090224, which clearly shows both Polymorph Form I and Polymorph Form II are distinct novel polymorphic forms.

The invention claimed is:

1. 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I, which is characterized by a powder X-ray diffraction pattern (PXRD) obtained by irradiation with Cu-Kα radiation which includes main peaks at 2-Theta° 5.9, 9.3, 9.8, 11.9, 13.7, 14.3, 15.0, 17.8, 18.2-19.3, 19.7, 22.6, 23.4-24.5 and 24.9+/−0.2.

2. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described in claim 1, which is further characterized by differential scanning calorimetry (DSC) in which it exhibits an endothermic event at about 169° C.

3. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described in claim 1, which is further characterized by an infrared (IR) spectrum (KBr) which shows absorption bands at 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556+/−2 $cm^{-1}$.

4. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II, which is characterized by a powder X-ray diffraction pattern (PXRD) obtained by irradiation with Cu-Kα radiation which includes main peaks at 2-Theta° 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6+/−0.2.

5. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II as described in claim 4, which is further characterized by differential scanning calorimetry (DSC) in which it exhibits an endothermic event at about 167-169° C.

6. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II, as described in claim 4, which is further characterized by an infrared (IR) spectrum (KBr) which shows absorption bands at 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555+/−2 $cm^{-1}$.

7. A pharmaceutical composition including 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in claim 1 or claim 4, together with one or more pharmaceutically acceptable excipients.

8. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form as described in claim 1 or claim 4 for use as a medicament.

9. A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I as described in claim 1, comprising the step of recrystallizing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid from ethyl acetate and a mixture of organic solvents which can be mixed with ethyl acetate.

10. A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II as described in claim 4, comprising the steps of placing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid on 110° C. or higher temperature, and then cooling down to room temperature under ambient conditions.

* * * * *